United States Patent
Devigne et al.

(10) Patent No.: US 9,562,899 B2
(45) Date of Patent: Feb. 7, 2017

(54) METHOD OF DETECTING OXA-048 CARBAPENEMASE PRODUCING BACTERIA

(71) Applicant: BIOMÉRIEUX, Marcy L'Etoile (FR)

(72) Inventors: Laurence Devigne, Vaux en Bugey (FR); Sandrine Ghirardi, Saint Genis les Ollières (FR); Gilles Zambardi, Chezeneuve (FR)

(73) Assignee: bioMérieux, Marcy L'Etoile (FR)

(*) Notice: Subject to any disclaimer, the term of this patent is extended or adjusted under 35 U.S.C. 154(b) by 0 days.

(21) Appl. No.: 14/412,315

(22) PCT Filed: Jul. 29, 2013

(86) PCT No.: PCT/FR2013/051819
§ 371 (c)(1),
(2) Date: Dec. 31, 2014

(87) PCT Pub. No.: WO2014/016534
PCT Pub. Date: Jan. 30, 2014

(65) Prior Publication Data
US 2015/0160211 A1    Jun. 11, 2015

(30) Foreign Application Priority Data

Jul. 27, 2012    (FR) ..................................... 12 57324

(51) Int. Cl.
| | | |
|---|---|---|
| C12Q 1/04 | (2006.01) |
| C12Q 1/68 | (2006.01) |
| C12Q 1/34 | (2006.01) |
| C12Q 1/18 | (2006.01) |
| G01N 33/569 | (2006.01) |
| C12Q 1/10 | (2006.01) |

(52) U.S. Cl.
CPC ........... *G01N 33/56911* (2013.01); *C12Q 1/04* (2013.01); *C12Q 1/045* (2013.01); *C12Q 1/10* (2013.01); *G01N 2333/986* (2013.01); *G01N 2458/00* (2013.01)

(58) Field of Classification Search
CPC .............. C12Q 1/34; C12Q 1/18; C12Q 1/04; C12Q 1/45; C12Q 1/68
USPC ...................... 435/18, 32, 34, 7.72
See application file for complete search history.

(56) References Cited

U.S. PATENT DOCUMENTS

| | | | | |
|---|---|---|---|---|
| 589,832 | A * | 9/1897 | Hook ...................... | H01H 3/16 200/61.41 |
| 5,989,832 | A * | 11/1999 | Trias et al. ................... | 435/7.2 |
| 8,753,875 | B2 * | 6/2014 | Frimodt-Moller ..... | C12Q 1/045 435/289.1 |
| 9,012,167 | B2 * | 4/2015 | Dallenne ................. | C12Q 1/04 435/18 |
| 9,241,947 | B2 * | 1/2016 | Reddy .................... | C07F 5/025 |
| 2007/0190592 | A1 * | 8/2007 | Black ....................... | C12Q 1/18 435/32 |
| 2009/0023170 | A1 * | 1/2009 | Citri .................... | G01N 33/9446 435/18 |
| 2009/0068696 | A1 * | 3/2009 | Frimodt-Moller .............. | 435/19 |
| 2009/0117601 | A1 * | 5/2009 | Yang-Woytowitz ............... | C12Q 1/04 435/18 |
| 2010/0256092 | A1 * | 10/2010 | Xia ........................ | A61K 31/33 514/64 |
| 2011/0003329 | A1 * | 1/2011 | Lovern .......................... | 435/34 |
| 2011/0065595 | A1 * | 3/2011 | Citri ........................ | C12Q 1/04 506/9 |
| 2011/0112059 | A1 * | 5/2011 | Hasan et al. .................. | 514/209 |
| 2011/0129869 | A1 * | 6/2011 | Rambach ................. | C12Q 1/10 435/29 |
| 2011/0245105 | A1 * | 10/2011 | Citri ........................ | C12Q 1/04 506/10 |
| 2012/0129180 | A1 * | 5/2012 | Kirveskari ............. | C12Q 1/689 435/6.12 |
| 2012/0196309 | A1 * | 8/2012 | Peaper ..................... | C12Q 1/04 435/18 |
| 2013/0089883 | A1 * | 4/2013 | Dallenne et al. ............... | 435/19 |

(Continued)

FOREIGN PATENT DOCUMENTS

| | | | | |
|---|---|---|---|---|
| EP | 2135959 | * | 12/2009 | ............... C12Q 1/04 |
| FR | 2956868 | * | 9/2011 | ............... C12Q 1/34 |

(Continued)

OTHER PUBLICATIONS

Cullmann, W et al, Chemotherapy, vol. 30, pp. 175-184, 1984, Influence of Spontaneous and Inducible B-Lactamase Production on the antimicrobial Activity of Recently developed B-lactam Compounds.*

Livermore, David M. et al, International Journal of Antimicrobial Agents, What remains against carbapenem-resistant Enterobacteriaceae? Evaluation of chloramphenicol, ciprofloxacin, colistin, fosfomycin, minocycline, nitrofurantoin, temocillin and tigecycline, vol. 37, 2011, pp. 415-419.*

Schultsz, C et al, Plasmid-Mediated Resistance in Enterobacteriaceae, Drugs, 2012, vol. 72(1), pp. 1-16.*

Wilkinson, Kathryn M. et al, Journal of Clinical Microbilogy, Sep. 201, vol. 50(9), pp. 3102-3104, published online ahead of print Jul. 3, 2012, Chromogenic Media for Carbapenemase Producers.*

Glupczynski, Y et al, International Journal of Antimicrobial Agens, vol. 39, Feb. 2012, pp. 168-172, Rapid emergence and spread of OXA-48 producing carbapenem-resistant Enterobacter5iaceae isolates in Belgian hospitals.*

ArMRL news, Health Protection Agency, Winter 2012, Issue 28 (2011-2012, published prior to Jul. 2012), pp. 1-5, Neil Woodford, Inferring OXA-48 carbapenemases, on p. 3 of 5.*

(Continued)

*Primary Examiner* — Albert Navarro
*Assistant Examiner* — Ginny Portner
(74) *Attorney, Agent, or Firm* — Oliff PLC

(57) ABSTRACT

A method of detecting and/or specifically identifying bacteria producing OXA-048-type carbapenemase in a biological sample, includes the steps of: (a) placing the biological sample likely to contain the bacteria in contact with a reaction medium including at least one chromogenic substrate to detect an enzymatic activity, and temocillin at a concentration equal to or greater than 150 mg/L, preferably between 200 and 500 mg/L, (b) incubating the sample in the medium to allow the bacteria to grow, and (c) detecting the strains corresponding to the OXA-48 carbapenemase producing bacteria. A culture medium as implemented in step (a) is also provided.

20 Claims, No Drawings

(56) References Cited

U.S. PATENT DOCUMENTS

2015/0031063 A1* 1/2015 Charretier .............. C12Q 1/04
                                                        435/23

FOREIGN PATENT DOCUMENTS

| WO | 2009/051838 | * | 4/2009 | .............. C12Q 1/04 |
| WO | 2010/010083 | * | 1/2010 | .............. C12Q 1/04 |
| WO | 2010/048511 | * | 4/2010 | .............. C12Q 1/18 |
| WO | 2010/067358 | * | 6/2010 | ............ G01N 33/50 |
| WO | 2012/003955 | * | 1/2012 | .......... C07D 477/06 |
| WO | 2012/070071 | * | 5/2012 | ............ A61K 31/34 |

OTHER PUBLICATIONS

Nordmann, P et al, 2012, Clinical Microbiology and Infection, European Society of Clinical Microbiology and Infectious Diseases,Identification and Screening of carbapenemase-producing Enterobacteriaceae, pp. 432-438, vol. 18.*

Girlich et al., "Value of the Modified Hodge Test for Detection of Emerging Carbapenemases in Enterobacteriaceae," Journal of Clinical Microbiology, Feb. 2012, vol. 50, No. 2, pp. 477-479.

Vrioni et al., "Comparative Evaluation of a Prototype Chromogenic Medium (ChromID CARBA) for Detecting Carbapenemase-Producing Enterobacteriaceae in Surveillance Rectal Swabs," Journal of Clinical Microbiology, Jun. 2012, vol. 50, No. 6, pp. 1841-1846.

Glupczynski et al., "Rapid Emergence and Spread of OXA-48-Producing Carbapenem-Resistant Enterobacteriaceae Isolates in Belgian Hospitals," International Journal of Antimicrobial Agents, 2012, vol. 39, pp. 168-172.

Nordmann et al., "Identification and Screening of Carbapenemase-Producing Enterobacteriaceae," Clinical Microbiology and Infection, May 2012, vol. 18, No. 5, pp. 432-438.

Poirel et al., "OXA-48-Like Carbapenemases: The Phantom Menace," Journal of Antimicrobial Chemotherapy, 2012, vol. 67, No. 7, pp. 1597-1606.

Livermore et al., "Temocillin Revived," Journal of Antimicrobial Chemotherapy, 2009, vol. 63, pp. 243-245.

Hartl et al., "Temocillin and Meropenem to Discriminate Resistance Mechanisms Leading to Decreased Carbapenem Susceptibility with Focus on OXA-48 in Enterobacteriaceae," Clinical Microbiology and Infection and Research Note, (2013) vol. 19, No. 5, pp. E230-E232.

Sep. 26, 2013 International Search Report issued in International Application No. PCT/FR2013/051819.

Bush et al., "Updated Functional Classification of β-Lactamases," Antimicrobial Agents and Chemotherapy, Mar. 2010, vol. 54, No. 3, pp. 969-976.

Orenga et al., "Enzymatic Substrates in Microbiology," Journal of Microbiological Methods, 2009, vol. 79, pp. 139-155.

Livermore et al., "What Remains Against Carbapenem-Resistant Enterobacteriaceae? Evaluation of Chloramphenicol, Ciprofloxacin, Colistin, Fosfomycin, Minocycline, Nitrofurantoin, Temocillin and Tigecycline," International Journal of Antimicrobial Agents, 2011, vol. 37, pp. 415-419.

Jan. 27, 2015 International Preliminary Report on Patentability issued in International Application No. PCT/FR2013/051819.

Nordmann et al., "Rapid Detection of Extended-Spectrum-β-Lactamase-Producing Enterobacteriaceae," Journal of Clinical Microbiology, Sep. 2012, vol. 50, No. 9, pp. 3016-3022.

* cited by examiner

METHOD OF DETECTING OXA-048 CARBAPENEMASE PRODUCING BACTERIA

The present invention relates to the field of microbiological analysis. More specifically, it relates to a method for detecting and/or identifying OXA-48 carbapenemase-producing bacteria.

The increase in the resistance to antibiotics of beta-lactam antibiotic type, such as penicillins and cephalosporins, makes the treatment of infections caused by Gram-negative bacterial strains complex. These antibiotics are therefore replaced with other broad-spectrum antimicrobials. Carbapenems have taken an important place among these broad-spectrum antimicrobials, in particular for treating hospitalized patients. Carbapenems are active against the majority of Gram-positive and Gram-negative aerobic bacteria and also against certain anaerobic bacteria.

However, an increasing number of carbapenem-resistant strains are appearing in hospitalized patients. In addition, it is essential to rapidly detect strains which exhibit carbapenemase activity so as to introduce, where appropriate, an antibiotic therapy which makes it possible to treat an infection appropriately, and so as to identify carrier patients in order to reduce the risk of propagation of these strains in care centers.

The nomenclature of beta-lactamases, which are bacterial enzymes for resistance to beta-lactam antibiotics, is not completely standardized. They are either categorized into four molecular classes (A to D) on the basis of their primary structure (Ambler classification), or into functional groups on the basis of the targeted substrates and of their resistance to inhibitors (for a review, see Bush and Jacoby, Antimicrobial Agents and Chemotherapy, 2010; 54 (3): 969-976).

The bacteria to which carbapenem resistance relates are, non-exhaustively, *Escherichia coli, Enterobacter cloacae, Enterobacter aerogenes, Citrobacter sp., Klebsiella pneumoniae, Klebsiella oxytoca, Pseudomonas aeruginosa, Providencia rettgeri, Pseudomonas putida, Stenotrophomonas maltophilia, Acinetobacter baumanii, Comamonas sp., Aeromonas sp., Morganella morganii, Enterococcus sp., Proteus mirabilis, Salmonella senftenberg, Serratia marcescens, Salmonella typhimurium*, etc.

These bacteria can produce various types of beta-lactamases capable of hydrolyzing carbapenems, or carbapenemases. Carbapenemases are very broad-spectrum beta-lactamases capable of inactivating almost all beta-lactam antibiotics. They are schematically divided up into three classes according to the Ambler classification:
  class A, also called serine carbapenemase, characterized by a variable inhibition by clavulanic acid and derivatives of boronic acid. The main representative is the KPC enzyme;
  class B, also called metallo-carbapenemase, characterized by an inhibition by cation-chelating agents, such as EDTA. The main representatives are the NDM, VIM and IMP enzymes;
  class D, which corresponds to the OXA-type beta-lactamases, among which is the variant OXA-48 which has the particularity of possessing carbapenemase activity. Other variants derived by point mutation from OXA-48 exist, although they are less frequent, and they retain this carbapenemase activity. Mention will be made of OXA-162, OXA-163, OXA-181, OXA-204 and OXA-232.

Metallo-beta-lactamases (MBLs) and *Klebsiella pneumoniae* carbapenemase (KPC) are prevalent in enterobacteria more particularly in North America, South America, Israel, Italy, Greece, India, China and Pakistan. Oxacillinase-48 (OXA-48) has recently been isolated in Turkey, in the Mediterranean basin and in Western Europe.

The carbapenemase genes are capable of being present in the chromosomes and/or in plasmids. Because of this presence in plasmid form, these enzymatic-type resistances are capable of disseminating very significantly and consequently present a major risk in terms of epidemiology.

In order to detect and/or identify carbapenem-resistant strains, it is possible to use molecular biology techniques which are very sensitive and have the advantage of allowing rapid identification of carbapenemase-producing enterobacterial strains. However, these methods are expensive and complex and are not routinely available in most laboratories.

For screening for, detecting and/or identifying carbapenemase-producing Enterobactriaceae (CPEs), methods based on culture are well known to those skilled in the art, They are based sequentially on isolation on a conventional medium of Mac-Conkey agar type or in tryptic soy broth made selective by adding a carbapenem or after the production of an antibiogram showing a non-sensitivity to a carbapenem. Where appropriate, disks impregnated with a carbapenem or Etest® strips (bioMërieux) can be used. Confirmation of the presence of carbapenemase by means of supplementary tests is necessary, among which tests mention will be made of: the modified Hodge test (CLSI M100-S22: Performance Standards for Antimicrobial Susceptibility Testing; Twenty-Second Informational Supplement. January 2012. Supplemental Table 2A-S2), and diffusion (or combined-disk) synergy tests in agar, using inhibitors combined with the carbapenem, for example EDTA for class B carbapenemases, phenylboronic acid for the detection of class A carbapenemases. The company Rosco proposes a multidisk method for detecting carbapenemase-producing bacteria using isolated strains (BioConnections KPC+MBL Confirm ID kit) and suggests adding a disk comprising 30 μg of temocillin for detecting the presence of an OXA-48 enzyme. However, this test shows that temocillin does not inhibit all KPC, AmpC and MBL strains and does not therefore enable, by itself, specific detection of OXA-48 strains. Thus, this prior art does not enable the specific detection of OXA-48 CPEs and requires a lengthy response period, of three days. Furthermore, these techniques are poorly suited to searching for CPEs in stool or rectal samples which are used to look for carriers in the context of the prevention of infections with multiresistant bacteria.

Other methods use commercial chromogenic media such as the Brilliance CRE medium (Oxoid®), the CHROMagar® KPC medium (CHROMagar™, Paris, France), the Colorex KPC equivalent medium (Biomed Diagnostics Inc.), or the applicant's chromID® ESBL or chromID® CARBA media. The latter medium proves to be capable of detecting a reference OXA-48 strain, but provided that the inoculum is large (approximately $10^7$ CFU/ml). Another medium (Super Carba (Nordmann et al., 2012, J. Clin. Microbiol., in press)) has been described, which enables reliable detection of OXA-48 producing CPEs, without however enabling their identification, nor a specific detection since the bacteria producing other types of carbapenemases are not inhibited. Furthermore, this medium has the drawback of a very short shelf life (approximately one week) which greatly limits its routine use and its industrialization.

Thus, none of these methods is at the same time sufficiently sensitive, specific and rapid for detecting OXA-48 strains, and no solution for improvement has been proposed.

Since the detection of OXA-48 strains is of real clinical and epidemiological interest, it remains to overcome the drawbacks of the existing media in this field.

In this regard, the present invention relates to a method for specifically detecting and/or identifying OXA-48 carbapenemase-producing bacteria in a biological sample, comprising the steps consisting in:

a) bringing the biological sample, which may contain said bacteria, into contact with a reaction medium comprising temocillin at a concentration greater than or equal to 150 mg/l, preferably between 200 and 500 mg/l, and a chromogenic substrate allowing the detection of a specific enzymatic activity, b) incubating the whole mixture so as to allow the bacteria to grow, and c) detecting the strains corresponding to the OXA-48 carbapenemase-producing bacteria.

Indeed, the applicant's studies have shown, surprisingly, that temocillin at high concentrations, greater than or equal to 150 mg/l, makes it possible to specifically distinguish OXA-48 CPEs. Preferentially, the temocillin is used at a concentration of between 150 and 500 mg/l. Thus, the method according to the invention enables a sensitive, specific and rapid detection (generally in less than 24 hours) of OXA-48 CPEs, while at the same time having the advantage of using a ready-to-use medium which has a long shelf life allowing its industrialization. Advantageously, the method according to the invention also enables the strains to be identified.

Temocillin is a 6-alpha-methoxy derivative of ticarcillin which is itself a penicillin, sometimes used in combination with clavulanic acid. It is described as an alternative treatment against multiresistant Enterobacteriaceae.

In vitro susceptibility tests have been carried out by Livermore et al. (International Journal of Antimicrobial Agents, 2011; 37: 415-419). They indicate a minimum inhibitory concentration (MIC)≥256 mg/l, which those skilled in the art interpret as meaning that the bacteria tested grow for the final temocillin concentration tested of 128 mg/l. These tests thus showed that 18/19 OXA-48 strains and 32/35 strains with a metallo-carbapenemase were resistant to temocillin. This dissuades those skilled in the art from using temocillin in a medium aimed at specifically detecting OXA-48.

The definitions hereinafter are specified in order to understand the invention more clearly.

The term "biological sample" is intended to mean an isolated small part or small amount of an entity for analysis. This sample may be a human or animal clinical sample, derived from a specimen of biological fluid, or a food sample, derived from any type of food, or a sample from the environment of food production or conversion. This sample may thus be liquid or solid. Mention may be made, in a nonlimiting manner, of a clinical sample of whole blood, serum, plasma, urine, feces or cerebrospinal fluid, or of nose, throat, skin, rectal or wound specimens, a food sample from water, from drinks such as milk or a fruit juice, from yogurt, from meat, from eggs, from vegetables, from mayonnaise, from cheese, from fish, etc, a food sample derived from an animal feed, such as, in particular, a sample derived from animal meals, or a surface or water control sample. Preferentially, according to the present invention, the sample is a clinical sample.

The specimen can be used as it is or, prior to analysis, can undergo a preparation of enrichment, dilution, extraction, concentration and/or purification type, according to methods known to those skilled in the art.

The term "reaction medium" is intended to mean a medium comprising all the elements required for the expression of a metabolism and/or for the growth of microorganisms. The reaction medium may be solid, semi-solid or liquid. The term "solid medium" is intended to mean, for example, a gelled or agar medium. Agar is the conventional gelling agent in microbiology for culturing microorganisms, but it is possible to use gelatin, agarose or other natural or artificial gelling agents, alone or in combination. A certain number of preparations are commercially available, for instance Columbia agar, Tryptic soy agar, Mac Conkey agar, Mueller Hinton agar or more generally those described in the Handbook of Microbiological Media (CRC Press).

The reaction medium may comprise one or more elements in combination, such as amino acids, peptones, carbohydrates, nucleotides, minerals, vitamins, etc. The medium may also comprise a dye. By way of indication, mention may be made, as dye, of Evans blue, neutral red, sheep blood, horse blood, an opacifier such as titanium oxide or kaolin, nitroaniline, malachite green, brilliant green, or one or more metabolic indicators, one or more metabolic regulators, etc.

The reaction medium may be a revealing medium or a culture and revealing medium. In the first case, the culture of the microorganisms is carried out before inoculation and, in the second case, the detection and/or identification medium also constitutes the culture medium. Identification means the classification of the microorganisms in a species or a group of interest.

Those skilled in the art can also use a biplate, or a dish of Petri dish type comprising two compartments, making it possible to easily compare two media, comprising various substrates or various selective mixtures, on which the same biological sample will have been deposited.

The reaction medium may comprise one or more selective agents. The term "selective agent" is intended to mean any compound capable of preventing or slowing down the growth of a microorganism other than the target microorganism. Without being limiting, a concentration of between 0.01 mg/l and 5 g/l is particularly suitable for the present invention. As selective agent, mention may be made of antibiotics, antifungals, bile salts, crystal violet, basic fuchsin, brilliant green, surfactants such as Tergitol™, etc. The term "antibiotic" is intended to mean any compound capable of preventing or slowing down the growth of a bacterium. They belong in particular to the groups of beta-lactam antibiotics, glycopeptides, aminosides, polypeptides, sulfamides, quinolones. By way of indication, mention may in particular be made of the antibiotics carbenicillin, ticarcillin, temocillin, formidacillin, cefotaxime, cefsulodine, ceftazidime, cefoxitin, ceftriaxone, cefpodoxime, aztreonam, ertapenem, faropenem, doripenem, vancomycin, gentamicin, trimethoprim, tobramycin, moxalactam, fosfomycin, D-cycloserine, polymyxin, colistin, quinolones such as nalidixic acid.

The term "antifungal" is intended to mean any compound capable of preventing or slowing down the growth of a yeast or of a mold. By way of indication, mention may in particular be made of amphotericin B, fluconazole, itraconazole, voriconazole, cycloheximide and flucytosine.

The term "chromogenic substrate" is intended to mean a substrate which makes it possible to detect an enzymatic or metabolic activity of the target microorganisms by virtue of a directly or indirectly detectable signal. For direct detection, this substrate may be bonded to a component acting as a label, which is fluorescent or colored (Orenga et al., 2009; J. Microbiol. Methods; 79(2):139-55). For direct detection, the reaction medium according to the invention may in addition comprise a pH indicator sensitive to the variation in pH induced by the consumption of the substrate and revealing the metabolism of the target microorganisms. Said pH indicator may be a chromophore or a fluorophore. As examples of chromophores, mention will be made of bromocresol purple, bromothymol blue, neutral red, aniline blue and bromocresol blue. The fluorophores comprise, for example, 4-methylumbelliferone, hydroxycoumarin derivatives or resorufin derivatives.

According to the present invention, the chromogenic substrate is preferentially chosen from substrates based on indoxyl(3-indoxyl, 5-bromo-3-indoxyl, 5-iodo-3-indoxyl, 4-chloro-3-indoxyl, 5-bromo-4-chloro-3-indoxyl, 5-bromo-6-chloro-3-indoxyl, 6-bromo-3-indoxyl, 6-chloro-3-indoxyl, 6-fluoro-3-indoxyl, 5-bromo-4-chloro-N-methyl-3-indoxyl, N-methyl-3-indoxyl, Aldol™, etc); on umbelliferone (4-methylumbelliferone, cyclohexenoesculetin, etc); on alizarin; on p-naphtholbenzene; on nitrophenol (ortho-nitrophenol, para-nitrophenol, etc); on hydroxyquinoline; on cathecol (cathecol, dihydroxyflavone, hydroxyflavone, etc); on resorufin; on chlorophenol red; on fluorescein; on aminophenol (para-aminophenol, dichloroaminophenol, etc); on naphthol (alpha-naphthol, 2-naphthol, naphthol-ASBI, etc); on aminocoumarin (7-amino-4-methylcoumarin, etc); on naphthylamide; on acridine (aminophenylacridine, etc); on aminophenoxazine (aminobenzophenoxazinone, aminopentylresorufin, etc); on aminostyryl(aminostyrylquinolinium, aminostyryllepidinium, etc).

By way of indication, the enzymatic activities targeted by the chromogenic substrates can belong to the hydrolase group, preferentially to the osidase, esterase or peptidase groups. Preferentially, the enzymatic activities targeted by the chromogenic substrates are chosen from: glucuronidase, glucosidase, galactosidase, ribosidase, esterase, sulfatase, phospholipase, aminopeptidase and deaminase.

By way of indication, the substrates used for the detection of a beta-glucuronidase activity may in particular be 4-methylumbelliferyl-beta-glucuronide, 5-bromo-4-chloro-3-indolyl-beta-glucuronide, 5-bromo-6-chloro-3-indolyl-beta-glucuronide, 6-chloro-3-indolyl-beta-glucuronide, Aldol™-beta-glucuronide, alizarin-beta-glucuronide, cyclohexenoesculetin-beta-glucuronide, or salts thereof.

The substrates used for the detection of a beta-galactosidase activity may in particular be 4-methylumbelliferyl-beta-galactoside, 5-bromo-4-chloro-3-indolyl-beta-galactoside, 5-bromo-6-chloro-3-indolyl-beta-galactoside, 6-chloro-3-indolyl-beta-galactoside, Aldol™-beta-galactoside, alizarin-beta-galactoside, cyclohexenoesculetin-beta-galactoside, or salts thereof.

The substrates used for the detection of an alpha-galactosidase activity may in particular be 4-methylumbelliferyl-alpha-galactoside, 5-bromo-4-chloro-3-indolyl-alpha-galactoside, 5-bromo-6-chloro-3-indolyl-alpha-galactoside, 6-chloro-3-indolyl-alpha-galactoside, or salts thereof.

The substrates used for the detection of a beta-glucosidase activity may in particular be 4-methylumbelliferyl-beta-glucoside, 5-bromo-4-chloro-3-indolyl-beta-glucoside, 5-bromo-4-chloro-3-indolyl-N-methyl-beta-glucoside, 5-bromo-6-chloro-3-indolyl-beta-glucoside, 6-chloro-3-indolyl-beta-glucoside, Aldol™-beta-glucoside, alizarin-beta-glucoside, cyclohexenoesculetin-beta-glucoside, nitrophenyl-beta-glucoside, dichloroaminophenyl-glucoside, or salts thereof.

The substrates used for the detection of an alpha-glucosidase activity may in particular be 4-methylumbelliferyl-alpha-glucoside, 5-bromo-4-chloro-3-indolyl-alpha-glucoside, 5-bromo-4-chloro-3-indolyl-N-methyl-alpha-glucoside, 5-bromo-6-chloro-3-indolyl-alpha-glucoside, 6-chloro-3-indolyl-alpha-glucoside, nitrophenyl-alpha-glucoside, or salts thereof.

The substrates used for the detection of a ribosidase activity may in particular be 4-methylumbelliferyl-beta-riboside, 5-bromo-4-chloro-3-indolyl-beta-riboside, 5-bromo-6-chloro-3-indolyl-beta-riboside, 6-chloro-3-indolyl-beta-riboside, alizarin-beta-riboside, nitrophenyl-beta-riboside, or salts thereof.

By way of indication, the substrates used for the detection of an esterase activity may in particular be the esters of saturated or unsaturated, linear fatty acids having between 6 and 14 carbons, preferentially between 7 and 9 carbons, and of 4-methylumbelliferone, 5-bromo-4-chloro-3-indoxyl, 5-bromo-6-chloro-3-indoxyl, 6-chloro-3-indoxyl, 5-bromo-3-indolyl, or alizarin, or salts thereof. Preferentially, they are chosen from 4-methylumbellifyl octanoate, 5-bromo-4-chloro-3-indoxyl octanoate, 5-bromo-6-chloro-3-indoxyl octanoate, 6-chloro-3-indoxyl octanoate, 5-bromo-3-indolyl octanoate, or alizarin octanoate.

The substrates used for the detection of a phospholipase activity may in particular be 4-methylumbelliferyl-phosphatidyl inositol, 4-methylumbelliferyl-phosphatidyl choline, 5-bromo-4-chloro-3-indolyl-phosphatidyl inositol, 5-bromo-4-chloro-3-indolyl-phosphatidyl choline, nitrophenyl-phosphatidyl inositol, nitrophenyl-phosphatidyl choline, or salts thereof.

The substrates used for the detection of an aminopeptidase activity may in particular be L-alanyl-7-amido-4-methylcoumarin, L-alanyldichloroamidophenyl, L-alanyl-7-amido-1-pentylphenoxazinone, L-alanyl-4-amidostyrylquinaldinium, or salts thereof.

The substrates used for the detection of a deaminase activity may in particular be L-tryptophan, L-phenylalanine, L-tyrosine and L-histidine.

The substrates used for the detection of a sulfatase activity may in particular be 4-methylumbelliferyl sulfate, 5-bromo-4-chloro-3-indoxyl sulfate, 5-bromo-6-chloro-3-indoxyl sulfate, 3-indoxyl sulfate, phenolphthalein disulfate, or salts thereof.

Preferentially, the chromogenic substrate is chosen from: 5-bromo-4-chloro-3-indoxyl-beta-D-glucopyranoside (X-glucoside), 5-bromo-6-chloro-3-indoxyl-beta-D-galactopyranoside (Magenta beta-Gal), 6-chloro-3-indoxyl-beta-D-glucuronide (Pink-beta-Gur), 5-bromo-4-chloro-3-indoxyl-N-methyl-beta-D-glucopyranoside (GreenA-beta-Glu), methyl-beta-D-glucopyranoside(methyl-beta-D-glucoside), lactose and L-tryptophan.

The reaction medium may also contain at least one cation-chelating agent, of EDTA type, for the purpose of complexing zinc which is a cofactor of class B carbapenemases, thus promoting their inhibition and thus being able to restore the activity of a beta-lactam antibiotic such as temocillin. Advantageously, the EDTA concentration is between 1.0 and 2.5 mmol/l. Other chelating agents may be mentioned by way of indication: dipicolinic acid, 2-mercaptoethanol, and phenanthroline derivatives.

The term "incubating" is intended to mean bringing to and maintaining for between 1 and 48 hours, preferentially between 4 and 24 hours, more preferentially between 16 and 24 hours, at an appropriate temperature, generally between 20 and 50° C., preferentially between 30 and 40° C.

The term "detecting" is intended to mean discerning with the naked eye or using an optical or digital apparatus the distance of growth of the target bacteria. Advantageously, when the medium used comprises a chromogenic substrate, the detection may also allow taxonomic identification of the target bacteria. The detection is carried out with the naked eye or using an optical or digital apparatus for the fluorescent substrates and for the colored substrates.

The term "specificity" is intended to mean the capacity of the method or of the reaction medium to give a negative result when the bacterial strain sought is not present. In other words, according to the present invention, a more specific identification corresponds to a reduction in the number of false positives associated with strains not expressing OXA-48 carbapenemase, without meaning to inhibit all of these strains.

The term "sensitivity" is intended to mean the capacity to give a positive result when the bacterial strain sought is present in the sample.

Thus, the present invention relates to a method for specifically detecting and/or identifying OXA-48 carbapenemase-producing bacteria in a biological sample, comprising the steps consisting in:

a) bringing the biological sample which may contain said bacteria into contact with a reaction medium comprising a chromogenic substrate, and temocillin at a concentration greater than or equal to 150 mg/l, preferably between 200 and 500 mg/l, b) incubating the whole mixture so as to allow the bacteria to grow, and c) detecting the strains corresponding to the OXA-48 carbapenemase-producing bacteria.

Advantageously, the chromogenic substrate makes it possible to detect an enzymatic activity and to identify the bacteria detected.

Advantageously, said reaction medium is a culture medium.

According to one particular embodiment of the invention, the reaction medium used in step a) also comprises a divalent-cation-chelating agent, of EDTA type, preferentially at a concentration of between 1.0 and 2.5 mM.

According to one particular embodiment of the invention, the medium used in step a) comprises at least one other chromogenic substrate which makes it possible to detect an enzymatic activity.

Preferentially, the enzymatic activity detected so as to allow the identification of the bacteria is chosen from esterase, glucosidase, galactosidase and glucoronidase activities.

Preferentially, the target bacteria capable of producing OXA-48 carbapenemases are Enterobacteriaceae.

Advantageously, the method according to the invention combines two reaction media, one comprising at least one chromogenic substrate and temocillin, the other comprising at least one chromogenic substrate and a carbapenem, preferentially faropenem. Preferentially, a dish of two-compartment Petri dish type, otherwise called a biplate, makes it possible to combine these two media. A comparison of the colonies present after incubation makes it possible to identify the strains corresponding to the carbapenem-resistant and/or OXA-48 carbapenemase-producing bacteria.

The present invention also relates to a ready-to-use culture medium for the specific detection and/or identification of OXA-48 carbapenemase-producing Enterobacteriaceae, comprising:

a nutritive agar base suitable for the growth of Enterobacteriaceae, temocillin at a concentration greater than or equal to 150 mg/l, preferably between 200 and 500 mg/l, and at least one chromogenic substrate.

Advantageously, said culture medium also comprises a divalent-cation-chelating agent, of EDTA type, preferentially at a concentration of between 1.0 and 2.5 mM.

Finally, the present invention relates to the use of temocillin at a concentration greater than or equal to 150 mg/l, preferentially at a concentration of between 200 and 500 mg/l, in an agar or liquid reaction medium, for specifically detecting and/or identifying OXA-48 carbapenemase-producing bacteria which may be included in a biological medium.

For the purposes of the present invention, the temocillin is in homogeneous phase in the reaction medium, in the presence of the sample. The temocillin is not impregnated on a disk or on a strip or on another independent container deposited on or in the reaction medium.

The aim of the examples developed below is to facilitate the understanding of the invention. They are given by way of explanation and could not limit the scope of the invention.

Example 1

Determination of the MICs with Respect to Temocillin for a Panel of CPE Strains (Using the Agar Dilution Method)

Strain Collection Used:

| Resistance profile | No. of strains |
|---|---|
| Amp C | 10 |
| BLSE | 10 |
| IMP | 13 |
| KPC | 12 |
| NDM-1 | 26 |
| Impermeability-mediated resistance (IR) | 10 |
| VIM | 16 |
| OXA-48 | 16 |

Reaction medium: the base is a chromLD™ CPS medium (bioMérieux, ref. 43821-43829), comprising a chromogenic substrate for beta-glucuronidase, a chromogenic substrate for beta-glucosidase, a chromogenic substrate for beta-galactosidase and a substrate for deaminase. Temocillin is added to this base medium at the concentrations indicated hereinafter.

Temocillin range tested: 50-150-200-300 mg/l (disodium temocillin, Eumedica SA, Manage, Belgium).

Method

The media are inoculated by depositing a spot: 1 µl of a microbial suspension in physiological saline at 0.5 McF, diluted to 1/10.

Incubation for 24 h at 37° C.

Reading after incubation for 24 hours. The medium with the smallest temocillin concentration on which a negative growth spot is obtained will be retained as the MIC. The spots having only 3 colonies or less or a total absence of growth were considered to be negative.

Results

| MIC | BLSE | KPC | NDM-1 | OXA-48 | IR* | AmpC | IMP | VIM |
|---|---|---|---|---|---|---|---|---|
| ≤50 | 8 | 8 | 25 | 1 | 8 | 10 | 12 | 9 |
| 150 | 0 | 1 | 1 | 0 | 2 | 0 | 0 | 5 |
| 200 | 0 | 0 | 0 | 0 | 0 | 0 | 0 | 1 |
| 300 | 0 | 0 | 0 | 0 | 0 | 0 | 0 | 0 |
| >300 | 2 | 3 | 0 | 15 | 0 | 0 | 1 | 1 |

*IR: strains with impermeability-mediated resistance to carbapenems

Conclusion

Most of the non-OXA-48 strains have MICs≤200. The majority of the OXA-48 strains have MICs>300. Only a few non-OXA-48 strains also have MICs>300.

Detection of strains producing an OXA-48 carbapenemase (with a temocillin concentration of 200 mg/l):

| | |
|---|---|
| Sensitivity | 93.8% |
| Specificity | 92.8% |

Temocillin therefore appears to be discriminating with respect to strains producing an OXA-48 carbapenemase starting from the concentration of 150 mg/l and very discriminating at 200 mg/l.

Example 2

Optimization of the Detection Specificity by Introducing Specific Inhibitors Inhibition of Class B Strains (NDM, VIM, IMP) by Adding EDTA Strain Collection Used:

| Resistance profile | No. of strains |
|---|---|
| AmpC | 10 |
| BLSE | 10 |
| IMP | 13 |
| KPC | 19 |
| NDM-1 | 27 |
| Impermeability-mediated resistance (IR) | 10 |
| VIM | 17 |
| OXA-48 | 15 |

Peptone Base:

Identical to that used to determine the temocillin MICs by agar dilution (example 1).

Temocillin range 50-150-200-300 mg/l.

For each temocillin concentration, the following concentrations of active EDTA will be tested in the form of disodium EDTA: 0, 1.77, 2.12, 2.47 and 2.83 mmol/l.
Method: identical to the method used in example 1.
Results:

Distribution of MICs obtained with a medium at 0 mmol/l of EDTA

| MIC | BLSE | KPC | NDM-1 | OXA-48 | IR | AmpC | IMP | VIM |
|---|---|---|---|---|---|---|---|---|
| ≤50 | 10 | 18 | 22 | 0 | 8 | 10 | 12 | 9 |
| 150 | 0 | 0 | 4 | 0 | 2 | 0 | 0 | 6 |
| 200 | 0 | 0 | 1 | 0 | 0 | 0 | 0 | 1 |
| 300 | 0 | 0 | 0 | 3 | 0 | 0 | 0 | 0 |
| >300 | 0 | 1 | 0 | 12 | 0 | 0 | 1 | 1 |

Distribution of MICs obtained with a medium at 1.77 mmol/l of active EDTA

| MIC | BLSE | KPC | NDM-1 | OXA-48 | IR | AmpC | IMP | VIM |
|---|---|---|---|---|---|---|---|---|
| ≤50 | 10 | 18 | 25 | 0 | 4 | 9 | 12 | 17 |
| 150 | 0 | 0 | 2 | 0 | 4 | 1 | 0 | 0 |
| 200 | 0 | 0 | 0 | 0 | 1 | 0 | 0 | 0 |
| 300 | 0 | 0 | 0 | 0 | 1 | 0 | 0 | 0 |
| >300 | 0 | 1 | 0 | 15 | 0 | 0 | 1 | 0 |

Distribution of MICs obtained with a medium at 2.12 mmol/l of active EDTA

| MIC | BLSE | KPC | NDM-1 | OXA-48 | IR | AmpC | IMP | VIM |
|---|---|---|---|---|---|---|---|---|
| ≤50 | 9 | 18 | 26 | 0 | 4 | 9 | 12 | 17 |
| 150 | 1 | 0 | 1 | 0 | 3 | 1 | 0 | 0 |
| 200 | 0 | 0 | 0 | 0 | 2 | 0 | 0 | 0 |
| 300 | 0 | 0 | 0 | 0 | 1 | 0 | 0 | 0 |
| >300 | 0 | 1 | 0 | 15 | 0 | 0 | 1 | 0 |

Distribution of MICs obtained with a medium at 2.47 mmol/l of active EDTA

| MIC | BLSE | KPC | NDM-1 | OXA-48 | IR | AmpC | IMP | VIM |
|---|---|---|---|---|---|---|---|---|
| ≤50 | 10 | 18 | 26 | 0 | 6 | 10 | 12 | 17 |
| 150 | 0 | 0 | 1 | 0 | 2 | 0 | 0 | 0 |
| 200 | 0 | 0 | 0 | 0 | 2 | 0 | 0 | 0 |
| 300 | 0 | 0 | 0 | 2 | 0 | 0 | 0 | 0 |
| >300 | 0 | 1 | 0 | 13 | 0 | 0 | 1 | 0 |

Distribution of MICs obtained with a medium at 2.83 mmol/l of active EDTA

| MIC | BLSE | KPC | NDM-1 | OXA-48 | IR | AmpC | IMP | VIM |
|---|---|---|---|---|---|---|---|---|
| ≤50 | 10 | 19 | 27 | 3 | 6 | 10 | 12 | 17 |
| 150 | 0 | 0 | 0 | 1 | 3 | 0 | 0 | 0 |
| 200 | 0 | 0 | 0 | 0 | 1 | 0 | 0 | 0 |
| 300 | 0 | 0 | 0 | 3 | 0 | 0 | 0 | 0 |
| >300 | 0 | 0 | 0 | 8 | 0 | 0 | 1 | 0 |

Conclusion: the class B CPEs of VIM and NDM type experience a decrease in their MIC in the presence of EDTA proportionally to the concentration used. On the other hand, EDTA appears to promote a slight increase in the MICs for the strains with impermeability-mediated resistance to carbapenems (IR).

Performance levels obtained for a temocillin concentration at 300 mg/l

|  | % sensitivity | % specificity |
|---|---|---|
| Medium at 0 mmol/l EDTA | 100 | 97.2 |
| Medium at 1.77 mmol/l EDTA | 100 | 98.1 |
| Medium at 2.12 mmol/l EDTA | 100 | 98.1 |
| Medium at 2.47 mmol/l EDTA | 86.7 | 98.1 |
| Medium at 2.83 mmol/l EDTA | 53.3 | 99.1 |

The introduction of EDTA allows an improvement in specificity, starting from 1.77 mmol/l, without degradation of the OXA-48 strain detection sensitivity if the concentration remains <=2.12 mmol/l.

Example 3

Evaluation of the Performance Level of a Defined Prototype Medium

Strain Collection Used:

| Resistance profile | Number of strains |
|---|---|
| BLSE | 2 |
| IMP | 1 |
| KPC | 3 |
| NDM-1 | 1 |
| IR | 3 |
| VIM | 1 |
| OXA-48 | 15 |

Method:

The media are prepared in 55 mm diameter Petri dishes. They are inoculated using a bacterial suspension in physiological saline at 0.5 McF for the non-OXA-48 strains and with a 1/100 and 1/10 000 dilution of a suspension at 0.5 McF for the OXA-48 strains. The inoculation consists of 3-quadrant streaking using a 10 µl calibrated loop: theoretical deposit of $10^4$ or $10^2$ CFU for the OXA-48 strains and of $10^6$ CFU for the strains not producing OXA-48.

The media are incubated at 37° C. The readings will be carried out after 18 and 24 hours of incubation.

The growth density, the colony sizes and also the coloration (color and strength) are evaluated.

Reaction medium identical to the base used for example 1. A selective system comprising a mixture of antibiotics and antifungals which is specific for Gram-positives, yeasts and Gram-negatives which are non-fermenting, and also cloxacillin and EDTA, is also added.

Temocillin range: 200, 300, 400 and 500 mg/l

A medium at 200 mg/l of temocillin is tested without selective system as indicated above.

Results at 24 Hours of Incubation:

| | Temocillin concentration in mg/l | | | | |
|---|---|---|---|---|---|
| No. of strains detected | 200 without selective system | 200 | 300 | 400 | 500 |
| OXA-48 deposit of $10^4$ CFU | 15/15 | 15/15 | 15/15 | 15/15 | 12/15 |
| OXA-48 deposit of $10^2$ CFU | 15/15 | 15/15 | 15/15 | 14*/15 | 9/15 |
| Non-OXA-48 deposit of $10^6$ CFU | 3**/13 | 3**/13 | 1/13 | 2***/13 | 2***/13 |

*including 3 strains with just 1 colony detected
**including 2 strains with just 1 colony
***including 1 strain with just 1 colony Conclusion: the addition of the selective system has no impact on the detection of the OXA-48 strains. The sensitivity tends to decrease slightly, in this reaction medium configuration, starting from 400 mg/l of temocillin.

The invention claimed is:

1. A method for specifically distinguishing OXA-48 carbapenemase-producing bacteria from other types of carbapenem-resistant bacteria in a biological sample, comprising:
    contacting the biological sample with a reaction medium that comprises temocillin at a concentration greater than or equal to 150 mg/l and at least one chromogenic substrate;
    incubating the reaction medium contacted with the biological sample so as to allow growth of OXA-48 carbapenemase-producing bacteria if present; and
    specifically detecting whether there is growth of OXA-48 carbapenemase-producing bacteria, to the exclusion of other types of carbapenem-resistant bacteria, on or in the reaction medium in order to discriminate OXA-carbapenemase-producing bacteria from other types of carbapenem-resistant bacteria,
    wherein the biological sample comprises carbapenem-resistant bacteria.

2. The method of claim 1, further comprising identifying the OXA-48 carbapenemase-producing bacteria grown on or in the reaction medium.

3. The method of claim 1, wherein the concentration of temocillin in the reaction medium is from 200 to 500 mg/l.

4. The method of claim 1, wherein the reaction medium further comprises a divalent-cation-chelating agent of EDTA type.

5. The method of claim 4, wherein the divalent-cation-chelating agent of EDTA type is at a concentration from 1.0 to 2.5 mmol/l.

6. The method of claim 1, wherein the OXA-48 carbapenemase-producing bacteria are *Enterobacteriaceae*.

7. The method of claim 1, wherein the reaction medium comprises more than one chromogenic substrate.

8. The method of claim 1, wherein the chromogenic substrate is an enzymatic substrate that includes a fluorescent or colored label.

9. The method of claim 1, wherein the chromogenic substrate is for detecting at least one enzymatic activity selected from the group consisting of esterase, glucosidase, galactosidase, and glucuronidase activities.

10. A method for detecting whether OXA-48 carbapenemase-producing bacteria and/or carbapenem-resistant bacteria are present in a biological sample, comprising:

contacting (i) a first portion of the biological sample with a first reaction medium, and (ii) a second portion of the biological sample with a second reaction medium;

incubating the first and second reaction media contacted with the first and second portions of the biological sample, respectively, so as to allow growth of OXA-48 carbapenemase-producing bacteria on or in the first reaction medium if present, and to allow growth of carbapenem-resistant bacteria on or in the second reaction medium if present; and detecting whether there is (i) growth of OXA-48 carbapenemase-producing bacteria, to the exclusion of other types of carbapenem-resistant bacteria, on or in the first reaction medium, and (ii) growth of carbapenem-resistant bacteria on or in the second reaction medium, wherein:

the first reaction medium comprises temocillin at a concentration greater than or equal to 150 mg/l and at least one chromogenic substrate; and the second reaction medium comprises a carbapenem and at least one chromogenic substrate.

11. The method of claim 10, wherein the carbapenem of the second reaction medium is faropenem.

12. The method of claim 10, wherein a biplate comprises the first and second reaction media.

13. The method of claim 10, further comprising identifying the OXA-48 carbapenemase-producing bacteria grown on or in the first reaction medium.

14. The method of claim 10, wherein the concentration of temocillin in the first reaction medium is from 200 to 500 mg/l.

15. The method of claim 10, wherein the first reaction medium further comprises a divalent-cation-chelating agent of EDTA type.

16. The method of claim 15, wherein the divalent-cation-chelating agent of EDTA type is at a concentration from 1.0 to 2.5 mmol/1.

17. A ready-to-use culture medium comprising:
a nutritive agar base suitable for growth of *Enterobacteriaceae*;
temocillin at a concentration greater than or equal to 150 mg/l;
a divalent-cation-chelating agent of EDTA type, and
at least one chromogenic substrate,
whereby the ready-to-use culture medium is formulated for the specific detection and/or identification of OXA-48 carbapenemase-producing *Enterobacteriaceae* to the exclusion of other types of carbapenem-resistant bacteria.

18. The culture medium of claim 17, wherein the concentration of temocillin is from 200 to 500 mg/l.

19. The culture medium of claim 17, wherein the divalent-cation-chelating agent of EDTA type is at a concentration from 1.0 to 2.5 mmol/l.

20. A biplate comprising (i) the culture medium of claim 17, and (ii) a second ready-to-use culture medium that comprises a carbapenem and at least one chromogenic substrate.

* * * * *